United States Patent [19]

Paal

[11] 4,142,892

[45] Mar. 6, 1979

[54] METHOD OF REDUCING THE DEFECT DENSITY IN A POSITIVE-WORKING PHOTORESIST LAYER USING A SALT OF IMIDAZOLINIUM

[75] Inventor: Gabor Paal, Stuttgart, Fed. Rep. of Germany

[73] Assignee: International Business Machines Corporation, Armonk, N.Y.

[21] Appl. No.: 799,048

[22] Filed: May 20, 1977

[30] Foreign Application Priority Data

Jun. 12, 1976 [DE] Fed. Rep. of Germany ....... 2626419

[51] Int. Cl.$^2$ .......................... G03C 5/00; G03C 1/60
[52] U.S. Cl. ........................................ 96/36; 96/36.2; 96/75; 96/86 P; 96/91 D; 96/115 R
[58] Field of Search ................. 96/36, 36.2, 75, 86 P, 96/91 D, 115 R

[56] References Cited

U.S. PATENT DOCUMENTS

| | | | |
|---|---|---|---|
| 2,859,112 | 11/1958 | Sus et al. | 96/91 D |
| 2,974,042 | 3/1961 | Sus et al. | 96/91 D |
| 3,615,532 | 10/1971 | Silver | 96/91 D |
| 3,637,644 | 1/1972 | Dunham et al. | 96/91 D |
| 3,661,582 | 5/1972 | Broyde | 96/36 |
| 3,827,908 | 8/1974 | Johnson et al. | 96/91 D |
| 3,873,316 | 3/1975 | Velten et al. | 96/91 D |
| 3,969,118 | 7/1976 | Stahlhofen et al. | 96/75 |
| 4,009,033 | 2/1977 | Bakos et al. | 96/36 |
| 4,036,644 | 7/1977 | Kaplan et al. | 96/36 |

*Primary Examiner*—Charles L. Bowers, Jr.
*Attorney, Agent, or Firm*—David M. Bunnell

[57] ABSTRACT

The density of defects formed during the exposure of a positive resist layer, due to the loss of photoresist in circular areas is reduced by the addition of an antistatic agent. The resist layer includes a phenol-formaldehyde resin and an o-diazoquinone photoactive compound and a suitable antistatic agent is a 2-alkyl-N-hydroxyethyl imidazolinium salt.

3 Claims, 1 Drawing Figure

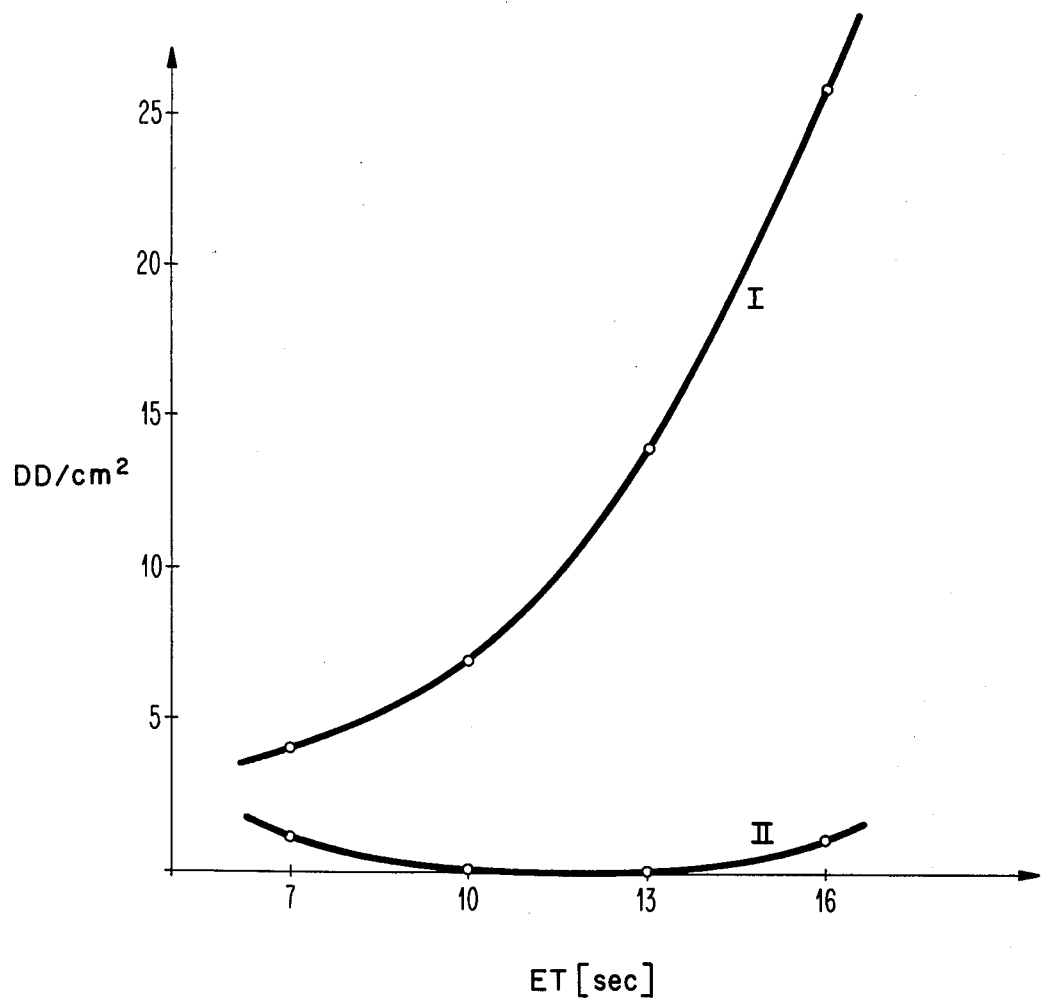

METHOD OF REDUCING THE DEFECT DENSITY IN A POSITIVE-WORKING PHOTORESIST LAYER USING A SALT OF IMIDAZOLINIUM

BACKGROUND OF THE INVENTION

In the production of monolithic circuits, photosensitive resist materials play an important part. The use of such photoresist materials in circuit technology is based on their suitability in permitting the "engraving" of circuit patterns of specific dimensions in a predetermined monolithic substrate material, as for instance silicon. This is effected by means of a photolithographic process where, by photolithographic means, a two-dimensional pattern corresponding to the circuit design is first imaged on the photoresist coated substrate surface by means of a suitable exposure mask. Through a subsequent developing process, the desired resist patterns are obtained on the substrate surface. By means of suitable processes, such as coating or etching, specific profiles can be formed on the substrate surface. In these processes, the photoresist serves as protective varnish system for those areas of the substrate surface that have not been bared by the proceding photolithographic process.

According to their interaction with light, photoresist systems are classified into negative-working and positive-working systems. A negative-working photoresist is a photoresist which after exposure is insoluble in a suitable solvent, whereas the unexposed resist areas are dissolved by the developer. As a result bared, unprotected areas are obtained on the substrate surface which correspond to the opaque dark areas on the photomask. Examples of negative-working resist systems are photoresist materials based on partially cyclized cis-1,4-polyisoprene with a di-azidobenzalalkyl-cyclohexanone as a photoinitiator. In a positive-working resist system the photoresist is altered under exposure in such a manner that it is subsequently soluble in the developer. The exposed areas of the resist film are removed during developing, and the bared unprotected areas on the substrate surface correspond to the transparent areas on the photomask. Examples of positive-working resist systems are photoresist materials based on phenol formaldehyde resins (Novolak type) with a suitable molecular weight distribution, which contain a photoactive compound, a so-called inhibitor, for instance the substituted diazoquinones such as are described for example, in U.S. Pat. Nos. 3,046,118; 3,046,121; 3,106,465; and 3,201,239.

Compared with negative-working resist materials, positive-working resist materials show some advantages. Their sensitivity with respect to oxygen, for example, is much lower than that of negative-working resist materials which facilitates their handling in photolithographic processes. Positive-working photoresist materials show a higher resolution of the exposure geometries than negative-working resist materials. This is highly desirable considering the precision and the importance of details required for semiconductor purposes. Finally, masks of positive-working resist material which are for instance used for making diffusion windows in a silicon dioxide layer on semiconductor wafers, are much more easily removable with a solvent mixture from the substrate after etching the oxide layer, than masks made of negative-working resist materials.

A disadvantage of positive-working resist materials is, however, that compared with negative-working resist materials they adhere more easily to the contact exposure masks used for exposure, so that defects appear in the resist images. To give an example: with the use of a frequently employed positive-working resist, AZ 1350 J resist of Shipley Comp. Inc., a resist pick-up in the order of 20 to 30 was counted on a contact exposure mask after ten exposures. It has been suggested to coat the contact exposure mask with a fluorinated methacrylate polymer. Thus, the previously given resist pick-up by the contact exposure mask could be reduced from about 30 to about 0 to 7.

Other possible means of avoiding the resist pick-up by the mask were examined, one of them performs the image-wise exposure of a layer of positive-working resist material with a small gap in the order of 10 to 50 $\mu$ between mask and photoresist layer (proximity printing). Another version is the use of a projection exposure process, where via optical imaging, an image of the mask is produced on the photoresist-covered wafer.

It has been found that in spite of the off-contact exposure used in both the proximity and projection printing defects are still present due to missing portions of the photoresist layer. In layers of positive-working resist material blanket exposed without a mask, defects of the same type were found, too. Consequently, these defects must be caused by some other mechanism than by resist pick-up by contact with the exposure mask.

The cause of the defects is now believed to be an increased mechanical tension in the photoresist layer which is generated by molecular nitrogen released during exposure, and an interaction of the photoresist layer with the surface of the insulating layer on which it is coated owing to the electrostatic charging thereof.

It is therefore the object of the invention to provide a process for reducing the density of defects which are produced during the off-contact exposure of a positive-working resist layer consisting of a phenol-formaldehyde resin and an o-diazoquinone photoactive compound with actinic radiation due to the loss of photoresist particles.

BRIEF SUMMARY OF THE INVENTION

The object of the invention is achieved by adding an antistatic agent to the photoresist composition which includes a phenol-formaldehyde resin and an o-diazoquinone sensitizer.

Advantageous, antistatic compounds are of the general formula:

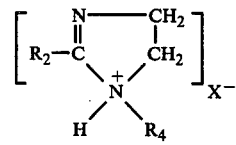

where $R_1$ is a hydroxyethyl group, $R_2$ is an alkyl group with 7 to 17 carbon atoms, and $X^-$ is an acid anion selected from the group consisting of acetate, oleate, stearate, and p-toluol-sulfonate. An aliphatic phosphoric acid ester can also be used as an antistatic agent.

DESCRIPTION OF THE DRAWING

The FIGURE is a graph comparing the defect density of unmodified resist with a resist of the invention.

DETAILED DESCRIPTION

The invention is described in detail in the following description and examples.

For etching windows into insulating thin layers, for instance into silicon dioxide layers produced thermally, pyrolytically, or by means of cathode ray sputtering, or into silicon nitride layers, the photoresist technology is applied in a known manner. A photoresist layer, applied on the insulating layer, is image-wise exposed and parts thereof are removed by developing after exposure. As described above, these processes increasingly use positive-working resist materials, because of their advantageous characteristics, and particularly the positive-working resists which contain a phenol-formaldehyde resin and an o-diazoquinone photoactive compound such as naphthoquinone-(1,2)-diazide sulfonic acid esters. After the image-wise exposure of approx. 1.0 to 2.0 $\mu$m thick photoresist layers circular defects were found, particularly in the exposed areas thereof, of a size of approx. 10 to 30 $\mu$m. As the defects, which are formed through the loss of photoresist in circular areas during exposure, are located mainly in the exposed areas of the positive-working resist layer, a large number of defects are removed during development. However, if a pattern is made with large exposed areas which are separated by small unexposed areas, the resist pattern is considerably damaged in that the photoresist particles flying off from the exposed areas during exposure tear off along portions of the photoresist layer in the adjacent unexposed areas and a defective etching mask is produced.

By means of the process disclosed by the invention the defect density in positive-working resist layers, comprising a phenol-formaldehyde resin and an o-diazoquinone photoactive compound can be reduced by adding an antistatic agent to the photoresist composition.

The modified positive-working resist is prepared by the addition of an effective amount, which is preferably about 1% by weight, of 2-alkyl-N-hydroxyethylimidazolinium acetate, oleate, stearate, or -p-toluene-sulfonate with a $C_7$ to $C_{17}$ alkyl group. Another applicable antistatic agent is the salt of an aliphatic phosphoric acid ester which is commercially available under the designation Tebestat ISG. The ester can also be added to the photoresist composition in a quantity of 1% by weight. The resist processing procedure used to form a patterned layer is conventional as is hereinafter described. The photoresist composition is filtered, and a thin photoresist film is applied by spin coating on a silicon wafer covered with a thermally generated silicon dioxide layer. The coated wafer is pre-baked in a known manner, for instance for 20 minutes at 85° C. in a nitrogen atmosphere. Subsequently, the photoresist film is image-wise exposed through a mask which is arranged at a distance of between 10 and 50 $\mu$m from the photoresist layer. The off-contact mode, image-wise exposure can also be carried out by means of a projection exposure process. The radiation source is, for instance, a 200 Watt mercury high pressure lamp. Exposure time is approx. 16 seconds. The exposed photoresist layer is developed in an aqueous alkaline developer, for instance, a mixture of sodium metasilicate, sodium phosphate, and sodium hydroxide. After development, the resist pattern bearing wafers are subjected in a known manner to another heating process, termed post-baking. The processed wafers can be etched, for instance, in a hydrofluoric etchant solution buffered with ammonium fluoride.

As indicated by the following embodiments, the defect density in the photoresist structures is considerably reduced by the process of the invention, and it is furthermore practically independent of the exposure time.

EXAMPLE 1

To AZ-1350 J photoresist of Shipley Comp. Inc., Newton, Mass., which is a photosensitive composition of an m-cresol formaldehyde resin and a 5-substituted diazonaphthoquinone sensitizer which is identified as mixed esters of 2,3,4-trihydroxybenzophenone and 1-oxo-2-diazonaphthalene-5-sulfonic acid, is added 1% by weight of 2-alkyl-N-hydroxyethyl imidazolinium acetate with a $C_7$ to $C_{17}$ alkyl group dissolved in ethylene glycol monoethyl ether acetate. The mixture is filtered under pressure through a filter with a pore diameter of 1 $\mu$m. The substrate materials used are wafers of monocrystalline silicon with a [111] orientation which are covered with a 4000 Å thick, thermally produced silicon dioxide layer. The wafers are precleaned in hot sulphuric acid and immediately before the coating with the photoresist layer they are treated with hexamethyl disilazane. After 5 seconds the wafers are rinsed with difluorodichloromethane. By means of this treatment, which is described in German Pat. Application P 19 15 085.7, the adherence of the photoresist on the silicon dioxide surface is improved.

Subsequently, 5 wafers are coated with unmodified photoresist, and another 5 wafers are coated with a photoresist modified with the 2-alkyl-N-hydroxyethyl imidazolinium acetate. The filtered photoresist is applied by spin coating at 3800 revolutions per minute to produce a layer thickness of approximately 2.0 $\mu$m. The coated wafers are prebaked for 20 minutes at 85° C. in a nitrogen atmosphere. Subsequently, the photoresist layer is image-wise exposed through a mask in an exposure device equipped with a 200 Watt mercury high pressure lamp. During the exposure a gap of between 10 and 50 $\mu$m (proximity printing), is maintained between mask and wafer. In the case of projection exposure printing a distance varying between some centimeters and 1 meter is maintained. The exposure time is approx. 16 seconds. During exposure, the sensitizer molecule rearranges to indene carboxylic acid, releasing nitrogen. Thus, the photoresist in the exposed areas becomes soluble in the aqueous alkaline developer mixture of sodium metasilicate, sodium phosphate, and sodium hydroxide. After developing, the wafers are post-baked conventionally and can subsequently be etched in a hydrofluoric acid etchant solution buffered with ammonium fluoride.

The defect density is determined by the visual inspection of 10 chips per processed wafer. The results are given in the following table and in FIG. 1 where the exposure time, ET, in seconds and the defect density, DD/cm$^2$, are presented relative to each other:

TABLE

| | | | | |
|---|---|---|---|---|
| Exposure Time [sec] | 7 | 10 | 13 | 16 |
| Defect Density [cm$^{-2}$] of Unmodified Photoresist | 4 | 7 | 14 | 25 |
| Defect Density [cm$^{-2}$] of Modified Photoresist | 1 | 0 | 0 | 1 |

The table shows that when the photoresist modified in accordance with the invention (curve II in the FIG. 1) is used compared with the same but unmodified photoresist (curve I), the defect density in each exposure time is strongly reduced and furthermore is practically independent of the exposure time. In the case of the unmodified photoresist, the defect density can also be reduced by reducing the exposure time. However, even with a strong underexposure it does not reach zero. The increasing of the defect density with increasing exposure time in the unmodified photoresist is explained by the greater amount of nitrogen except that which is released owing to the higher conversion of the photoactive compounds.

EXAMPLE 2

The process of Example 1 was repeated, the photoresist was modified with 1% by weight of other 2-alkyl-N-hydroxyethyl imidazolinium esters which were the oleate, stearate, and -p-toluol sulfonate where the alkyl group is $C_7$ to $C_{17}$. It was found that the presence of these additives considerably reduced the defect density caused by the loss of photoresist during exposure.

EXAMPLE 3

Example 1 was repeated except that instead of the imidazolinium acetate the salt of an aliphatic phosphoric acid ester, commercially available under the name Tebestat ISG was added to the photoresist in a quantity of 1% by weight. It was found that this compound also considerably reduces the defect density.

What is claimed is:

1. In a process for forming a resist mask, in which a positive working photoresist layer comprising a phenol-formaldehyde novolak resin and a photosensitive o-diazoquinone sulfonic acid ester, is patternwise exposed to actinic radiation and the exposed portion is removed by an aqueous alkaline developer, the improvement which comprises: reducing the defect density caused by the loss of resist during exposure by including in said layer, prior to exposing the layer, an effective amount of a compound of the general formula:

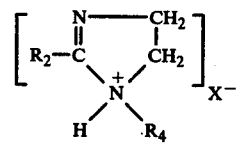

where $R_1$ is a hydroxyethyl group, $R_2$ is an alkyl group with 7 to 17 carbon atoms, and $X^-$ is an acid anion selected from the group consisting of acetate, oleate, stearate, and p-toluol-sulfonate.

2. The method of claim 1, wherein 2-alkyl-N-hydroxyethyl-imidazolinium acetate is added to the photoresist composition.

3. The method of claim 1, wherein the compound is added in a quantity of about 1% by weight of the photoresist composition.

* * * * *